United States Patent [19]

Adair et al.

[11] Patent Number: 4,744,757
[45] Date of Patent: May 17, 1988

[54] FIXED PARTIAL DENTURES AND METHOD OF MAKING

[75] Inventors: Peter J. Adair, Boston, Mass.; Vincent T. Cammarato, Milford, Del.; David G. Grossman, Corning, N.Y.

[73] Assignee: Corning Glass Works, Corning, N.Y.

[21] Appl. No.: 713,837

[22] Filed: Mar. 20, 1985

[51] Int. Cl.⁴ ............................................. A61C 13/12
[52] U.S. Cl. .................................... 433/180; 433/181; 433/183
[58] Field of Search ............... 433/180, 181, 182, 183

[56] References Cited

U.S. PATENT DOCUMENTS

| | | | |
|---|---|---|---|
| 1,475,808 | 11/1923 | Foster | 433/180 |
| 2,129,861 | 9/1938 | Morton | 433/219 |
| 3,091,032 | 5/1963 | Hirshhorn | 433/183 |
| 3,530,582 | 9/1970 | Weissman | 433/219 |
| 4,189,325 | 2/1980 | Barrett et al. | 433/203.1 |
| 4,431,420 | 2/1984 | Adair | 433/199.1 |
| 4,472,142 | 9/1984 | Gedzelman | 433/170 |

FOREIGN PATENT DOCUMENTS

| | | | |
|---|---|---|---|
| 25419 | 3/1981 | European Pat. Off. | 433/180 |
| 601836 | 8/1934 | Fed. Rep. of Germany | 433/183 |

OTHER PUBLICATIONS

UDA Brochure (Universal Dental Anchorage), 10 pages.

*Primary Examiner*—John J. Wilson
*Attorney, Agent, or Firm*—Clinton S. Janes, Jr.

[57] ABSTRACT

This invention is concerned with preparing fixed partial dentures consisting of abutment crowns and pontics connected through male/female attachments and being sealed together by means of a joining medium. In the most preferred embodiment, the parts of the dentures are formed from machinable glass-ceramic materials and the joining medium is curable through exposure to visible light radiation.

20 Claims, 3 Drawing Sheets

FIXED PARTIAL DENTURES AND METHOD OF MAKING

BACKGROUND OF THE INVENTION

This invention relates to the fabrication of fixed partial dentures (bridges) to replace missing teeth in the anterior and posterior areas of the mouth.

Fixed partial dentures have been fabricated from a wide variety of materials including ceramics, metals, plastics, and combinations of those materials. For example, bridges have been formed having an all metal construction, an all ceramic body (aluminous porcelain, spinel ceramics), a laminate of porcelain fused onto metal, and a laminate of acrylic bonded to metal. Each of those constructions exhibits certain advantages and is subject to inherent disadvantages. Nevertheless, one problem which has plagued all of those materials has involved fitting of the prosthesis in a patient's mouth.

In general, fixed partial dentures have comprised at least three parts, viz., two abutment crowns and a pontic therebetween. In fabricating a bridge, an impression is made of the area in the patient's mouth, a cast is prepared, and a dental technician then fashions a bridge therefrom. Where metal materials are employed, the three parts may be formed as an integral unit or the parts soldered or otherwise joined into a single unit. Where ceramic materials are involved, the components are typically assembled at the dental laboratory and delivered to the dentist as a single unit. A low temperature fusing solder glass (a dental porcelain) or other sealing means is used to surround the other aluminous porcelain or other ceramic components.

Because the impression and/or die prepared therefrom may not exactly represent the precise location of the abutment teeth and/or because the abutment teeth may move between the time the impression is made and the finished bridge is fitted in the patient's mouth, often the appliance will not fit properly. Thus, the customary mode of attachment has involved simple butt sealing or, occasionally, sealing by means of a dovetail or tongue-and-groove configuration. Such forms of attachment do not permit adjustments in the overall geometry of a appliance or in the profile of the individual parts to be quickly and readily performed. Accordingly, when the dentist notes inaccuracies in the fitting to the abutment teeth in the patient's mouth, the common practice is to return the bridge to the dental technician for the necessary alterations. Not infrequently, the metal appliance frame must be separated, the required adjustments made, and the parts re-soldered. As can be appreciated, those circumstances demand at least one further visit by the patient to the dentist's office to insure proper fitting.

Fixed partial dentures have been fabricated which have been asserted by their designers as permitting greater precision in fit to be achieved. For example, a dovetail or tongue-and-groove attachment has been designed wherein the joint is not permanently sealed together, thereby permitting vertical movement in the joint but lateral motion is constrained. Other types of precision attachments have been fashioned but none of the designs thereof has permitted sufficient omni-directional movement of contiguous appliance parts to be of any significant use in making adjustments.

Therefore, the principal objective of the present invention was to design a means for attaching the parts of a fixed partial denture together which permits adjustments to be made quickly and readily, thereby insuring proper fitting of the bridge in a single visit by the patient to the dentist's office.

GENERAL DESCRIPTION OF THE INVENTION

The instant invention is directed to the manufacture of fixed partial dentures for replacing missing teeth. The bridges are fabricated from abutment crowns and pontics that are connected by means of male/female attachments. In certain denture designs, the male connector will extend through and beyond the pontic. In other designs, the length thereof will not exceed about 75% and, most preferably, not exceed about 50% of the mesial-distal length of the pontic. The female portion(s) of the attachment(s) is typically, but not necessarily, located solely within the pontic and the male connector(s) is normally, but not necessarily, integral with the abutment crown. The parts are assembled in the patient's mouth and then joined together into a unitary structure with a joining medium.

Whereas fixed partial dentures can be composed of several parts, the invention will be illustrated by means of FIGS. 1-5.

FIG. 1 schematically represents a two-piece prosthesis. As is pictured there, 1 indicates an abutment crown having male connector 2 integral therewith and extending into cavity 3 of pontic 4, cavity 3 comprising the female portion of the attachment. In this embodiment, pontic 4 is integral with abutment crown 5.

FIG. 2 schematically depicts a three-piece appliance. Thus, 6 represents an abutment crown having male connector 7 unitary therewith and extending into female portion of the attachment 8 of pontic 9. Pontic 9 is a separate part which is cemented to abutment crown 10.

FIG. 3 schematically illustrates another three-piece bridge. As shown there, 10 represents an abutment crown having male connector 11 integral therewith and extending into cavity 12 of pontic 13. 14 indicates another abutment crown which has male connector 15 unitary therewith and extending into cavity 16 of pontic 13. Hence, FIG. 3 illustrates the use of double attachment through two male connectors in two female portions of the pontic.

FIG. 4 schematically illustrates yet another embodiment of a three-piece appliance. As pictured there, 17 depicts an abutment crown having pontic 18 integral therewith. Pontic 18 contains cavity 19, a female portion of the attachment. In like manner, 20 represents an abutment crown having pontic 21 unitary therewith. Pontic 21 contains cavity 22, another female portion of the attachment. Male connector 23 extends into cavities 19 and 22. Hence, this inventive embodiment utilizes two female portions and one male connector in the attachment.

FIG. 5 schematically represents a four-piece embodiment of the invention. Thus, 24 indicates an abutment crown containing cavity 25, a female portion of the attachment. In like manner, 26 represents an abutment crown containing cavity 27, another female portion of the attachment. Pontic 28 contains cavity 29, the third female portion of the attachment. Male connector 30 extends through and beyond cavity 29 and into cavities 25 and 27. Hence, three female portions and one male connector comprise this embodiment.

Most desirably, the male connector and the corresponding female portion will have a substantially cylindrical outline, although an oval or other curved geometry can be operable. A cylindrical configuration permits unlimited rotation of the parts, whereas an oval or other non-circular profile partially restrains rotary movement. Sharp corners, such as are present in a square or triangular outline, are not as desirable since rotation of the parts is inhibited.

The use of the inventive male/female attachment means also permits lateral movement of the parts prior to their being fixedly bonded into a unitary structure. This feature provides another degree of freedom in adjusting the bridge to fit into a patient's mouth. For example, that movement can compensate for any drift of a patient's teeth between the time the impression was made to prepare the bridge and the time of fitting the appliance into the patient's mouth.

Because of the degrees of freedom of movement provided by the inventive attachment means and the fact that the parts of the fixed partial denture are bonded together with a joining medium, assembly of the parts and precise fitting to a patient's mouth can be accomplished in a single visit to the dentist's office.

The inventive method is operable in fabricating prostheses from any of the many materials that are currently employed in the fabrication thereof. For example, a two-piece bridge of the type illustrated in FIG. 1 was cast from OPTION®, a dental palladium alloy marketed by The J. M. Ney Company, Bloomfield, Conn. However, the inventive method is especially suitable for use in bridges prepared from glass-ceramic materials. Because glass-ceramics are prepared through the heat treatment of precursor glass bodies, the ready formability of glass melts is advantageous in obtaining, as for example by casting, the desired complex shapes of abutment crowns with male connectors integral therewith and pontics having cavities therein. Hence, all parts of the denture can be composed of the same glass-ceramic composition. Alternatively, where desired, the male portions of the inventive bridges may be composed of one material and the remainder thereof of another. For example, the male portions may be fabricated from such diverse materials as metals, ceramics, plastics, or composites, such as fiber reinforced glasses, glass-ceramics, and metals, and the abutments and pontics formed from a like material or another metal, ceramic, plastic, or fiber reinforced glass, glass-ceramics, or metal.

The possible utility of glass-ceramic materials in the formation of dental crowns and inlays was conjectured by W. T. McCulloch in "Advances in Dental Ceramics," *British Dental Journal*, Apr. 16, 1968, pages 361–5. The writer formed teeth from glass-ceramics having base compositions within the $Li_2O-ZnO-SiO_2$ system nucleated with silver or a metal phosphate.

More recently, U.S. Pat. No. 4,189,325 described the use of glass-ceramics in dental restorations having base compositions within the $Li_2O-CaO-Al_2O_3-SiO_2$ system nucleated with platinum and $Nb_2O_5$.

Still more recently, U.S. Pat. No. 4,431,420 disclosed machinable glass-ceramic materials, suitable for use in dental restorations, containing tetrasilicic fluormica as the predominant crystal phase and having base compositions within the $K_2O-MgO-SiO_2-F$ system with $Al_2O_3$ and/or $ZrO_2$ being optionally present. Because of their physical properties, their resistance to staining and chemical attack in an oral environment, and their close similarity in appearance to tooth enamel, dental crowns are currently being fabricated from those materials. As recorded in that patent, the compositions of those glass-ceramics consist essentially, expressed in terms of weight percent on the oxide basis, of:

| $K_2O$ | 10–18 | $Al_2O_3$ | 0–2 |
|---|---|---|---|
| MgO | 14–19 | $ZrO_2$ | 0–7 |
| $SiO_2$ | 55–65 | F | 4–9 |

Glass bodies prepared from those compositions can be crystallized in situ to glass-ceramics by heat treatment at temperatures between about 1050°–1150° C.

The properties of those glass-ceramics rendering them especially useful for dental restorations also make them the most preferred materials for the inventive fixed partial dentures. In particular, their ready machinability with hand instruments permits modifications in the geometry of the appliance parts to be easily made. Furthermore, the compositions thereof can allow the transmission of ultraviolet and visible light radiation therethrough, the importance of which is described below.

The use of joining media to bond together the parts of a bridge into a unitary structure is advantageous in achieving a customized fit in a patient's mouth. Hence, the appliance parts with the joining medium applied at the proper locations can be assembled outside of the patient's mouth, the assembly placed inside the patient's mouth, the parts moved to accommodate precisely to the contour of the mouth, and the medium cured in place. The use of joining media in fixed partial dentures is also advantageous from a second standpoint, especially when the prosthesis parts are prepared from a ceramic or glass-ceramic. That is, the elastic modulus of the medium may be considerably less than that of the appliance parts such that it can act as a stress absorber, i.e., it provides some "give".

Whereas any of the conventional time-setting dental cements, such as zinc phosphates, glass ionomers, polycarboxylates, etc., are operable in the inventive bridges, the most preferred joining media are composite resins which can be cured upon exposure to radiation, e.g., ultraviolet and/or visible light radiation. Such joining media and quite apparently useful only with materials which permit the transmission of those radiations therethrough. The machinable glass-ceramics of U.S. Pat. No. 4,431,420 discussed above are sufficiently translucent to allow the use of those cements.

Since such joining media are subject to no time-setting constraints, they permit the dentist to insure an optimum fit between the prosthesis and a patient's mouth. Hence, the appliance parts with the radiation curable material applied at the proper locations can be assembled in the patient's mouth and the parts moved to achieve the proper fit without concern that the medium will set before the desired precise fit is secured. After the optimum fit has been achieved, the bridge will be exposed to the radiation for a brief period while in the patient's mouth to initiate curing of the cement in place. That practice insures that fit of the prosthesis is maintained. Thereafter, the appliance may be removed from the mouth and finish cured outside thereof and then replaced. If desired, the prosthesis may simply be set in the mouth to achieve the proper fit, carefully removed therefrom, and the entire cure conducted outside the mouth. Because of a possible hazard to the patient through exposure to ultraviolet radiation, the most preferred joining media are composite resins which are cured under high intensity visible light.

PRIOR ART

U.S. Pat. No. 2,129,861 describes the fabrication of a metal bridge comprising a rigid attachment at one end thereof to an anchoring tooth and a movable ball and socket attachment at the other end of the bridge to the other anchoring tooth. The connecting means consisted of a separate metal lock pin composed of a shank portion with a ball on one end thereof, the ball being movably embedded in an anchor tooth. Hence, the final bridge is not composed of units fixedly bonded to each other. Furthermore, there is no mention of a male connector which is integral with an abutment crown, of glass-ceramic materials, or of either time-setting or radiation-curable joining media.

U.S. Pat. No. 2,227,735 issued to the same patentee as U.S. Pat. No. 2,129,861, is stated to be founded in improvements upon the invention of the earlier patent. Hence, the mechanism of a ball and socket movable attachment means is again present; the inventive improvements residing in a modification in the geometry of the lock pin shank and the application of an anti-flux film to the ball of the pin.

U.S. Pat. No. 2,808,648 is directed to the fabrication of spring clamp joints for releasibly securing partial dental prostheses to a pillar tooth. The connecting means comprises a separate spring clamp device, such that the prosthesis does not consist of units fixedly bonded together. Again, no reference is made to a male connector which is integral with an abutment crown, to glass-ceramic materials, or to time-setting or radiation-curable joining media.

U.S. Pat. No. 3,530,582 refers to U.S. Pat. No. 2,129,861 above; the improvement thereupon residing in the use of a lock pin having a ball on each end of the pin instead of only on one end, each ball being movably embedded in an anchor tooth. Yet again, there is no mention of a bridge composed of units fixedly attached to each other, of a male connector which is integral with an abutment crown, of glass-ceramic materials, or of either time-setting or radiation-curable joining media.

U.S. Pat. No. 4,472,142 discloses the fabrication of a removable partial denture utilizing an attachment means involving a cylindrical pin having one end attached to the proximal surface of a crown and the other end removably retained in a hollow tubular member. The hollow tubular member is frictionally and rotatably mounted at one end in the bottom of the base of the denture which holds the artificial tooth adjacent the abutment tooth. The other end thereof has an axial slot in the wall of sufficient length and width to enable the pin to be inserted into the tubular member with slight flexure of the walls of the slot. The slot walls thus hold the pin within the member. The concept of a removable denture is contrary to a bridge fixedly attached to anchor teeth. There is no reference to glass-ceramic materials or to the use of time-setting or radiation-curable joining media.

DESCRIPTION OF THE PREFERRED EMBODIMENTS

As has been explained above, the most preferred materials from which the individual parts of the inventive dentures are fashioned are the glass-ceramics disclosed in U.S. Pat. No. 4,431,420. Also, the most preferred joining media are composite resins which are cured upon exposure to high intensity visible light radiation. With those two factors in mind, the invention will be described with specific reference to FIG. 1.

A batch for a glass having the following approximate composition, expressed in terms of parts by weight on the oxide basis, was melted. Because it is not known with which cation(s) the fluoride is combined, it is simply recorded as $MgF_2$, the batch ingredient utilized to supply the fluoride content.

| $SiO_2$ | 64.0 | $MgF_2$ | 9.7 |
|---|---|---|---|
| MgO | 11.9 | $ZrO_2$ | 5.0 |
| $K_2O$ | 14.4 | | |

Inasmuch as the sum of the individual ingedients only slightly exceeds 100, for all practical purposes the reported values may be deemed to reflect approximate weight percent.

Figure 1:
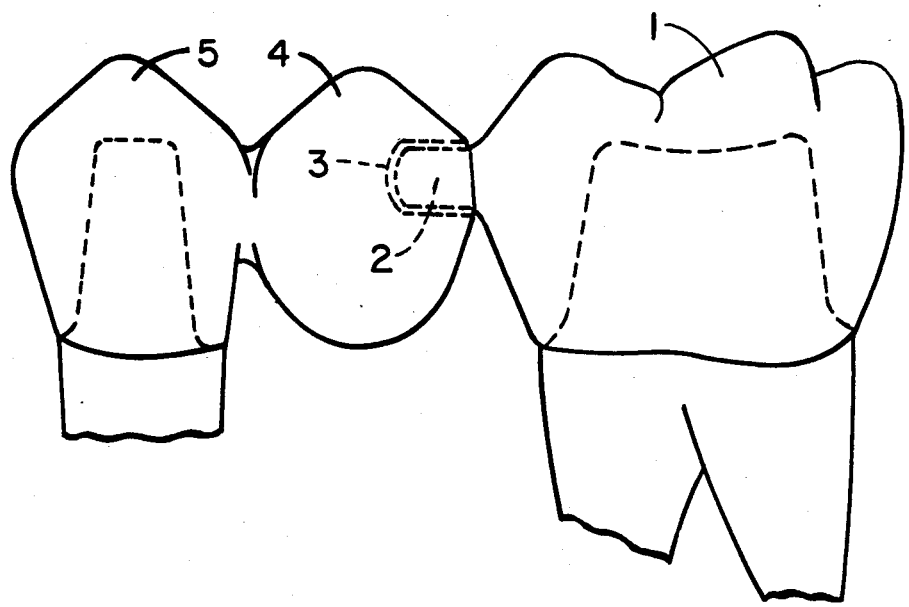
FIG. 1 is a schematic representation of a two-part, fixed partial denture comprising one illustrative embodiment of the present invention.
Figure 2:
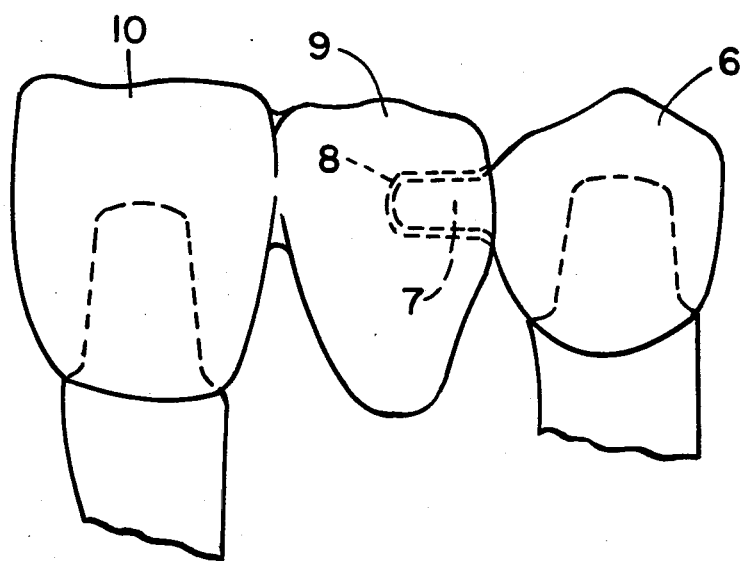
FIGS. 2–4 are schematic representations of three-part, fixed partial dentures comprising other illustrative embodiments of the present invention.
Figure 3:
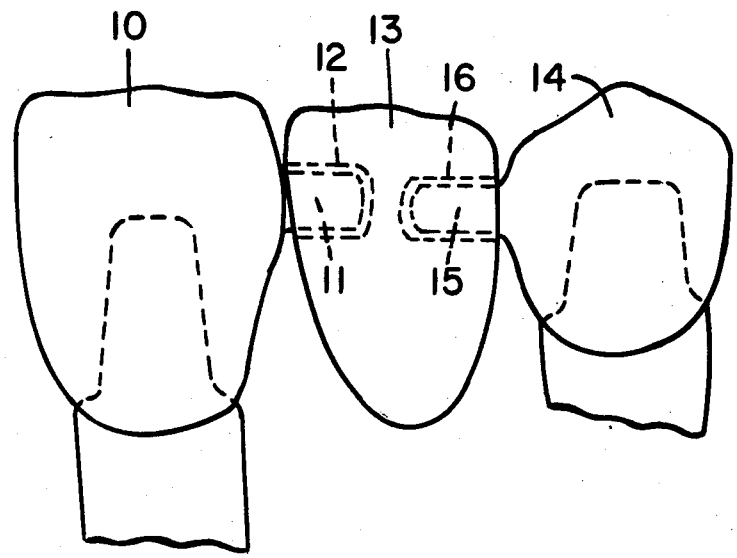
Figure 4:
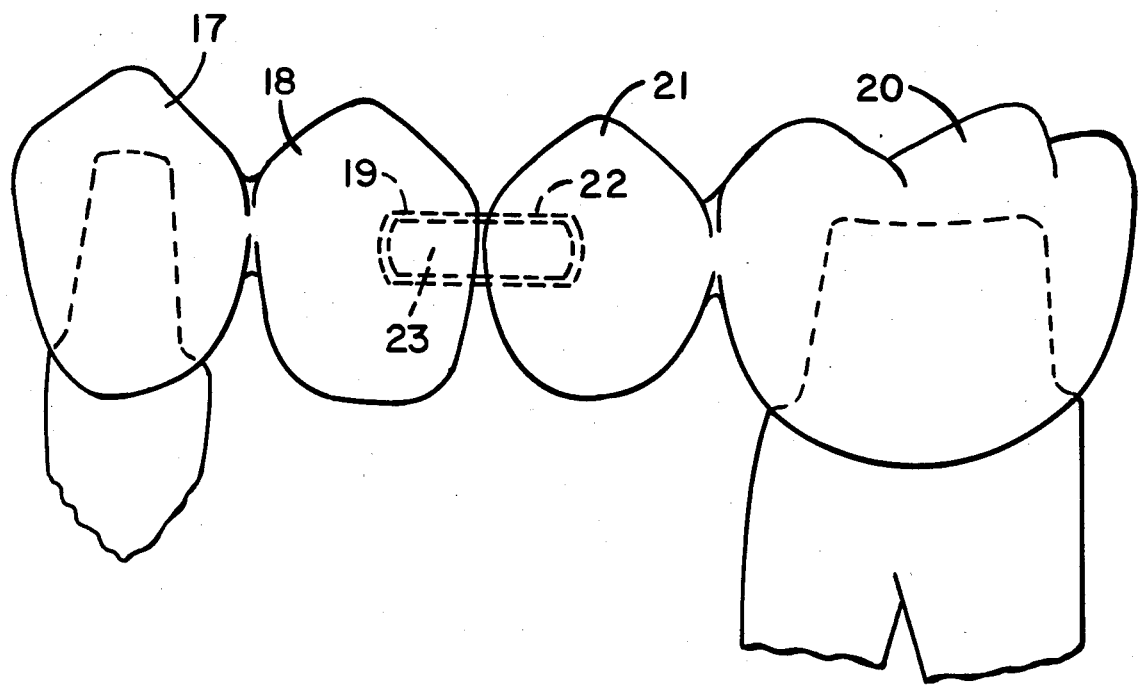
Figure 5:
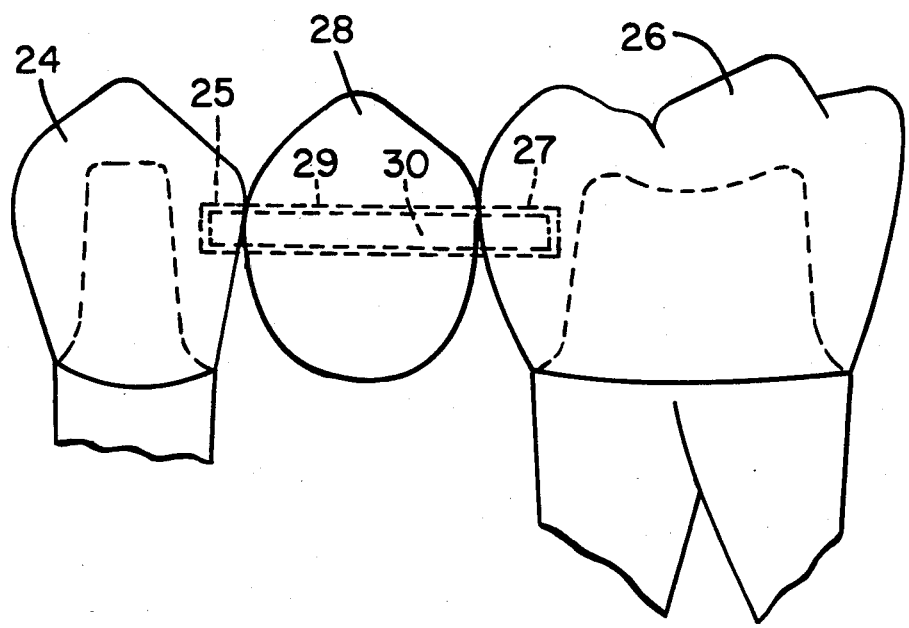
FIG. 5 is a schematic representation of a four-part, fixed partial denture comprising another illustrative embodiment of the present invention.

The melt was cast into two refractory investments, the cavities of which being designed to produce the proper geometries for parts 1 and 5 of the bridge depicted in FIG. 1. The resultant glass shapes were subsequently crystallized in situ to glass-ceramics through heat treatment according to the following schedule: heating at a rate of about 200° C./hour to 1075° C., holding at that temperature for about six hours, and then cooling to room temperature, desirably at a rate of about 200° C./hour.

The glass-ceramic parts were fitted to a die, apparent inaccuracies in the contour of the parts rectified, and surface tinting of the parts undertaken where desired, all according to standard dental laboratory techniques employed by laboratories using the commercially-available DICOR ™ procedures licensed by Dentsply International, Inc., York, Pa. The ready machinability of the glass-ceramic enables corrections in surface contour to be made with relative ease. The parts were then assembled in a patient's mouth. After any necessary adjustment, a visible light curing resin will be inserted within the female attachment and/or applied onto the male connector, the male connector will be introduced into the female attachment, the so-assembled interconnected parts placed upon their respective abutment teeth, and then exposed to a high energy source of visible light for a period of time adequate to develop a sufficient depth of cure in the resin.

The resin used was Prisma-Fil ®, a visible light cure composite resin marketed by L. D. Caulk Company of Milford, Del. That resin was diluted slightly with Prisma-Bond ®, an unfilled visible light cure resin also marketed by L. D. Caulk Company.

The source of high intensity visible light was a Prisma-Lite ® curing light, also marketed by L. D. Caulk Company, having an output of about 387–460 milliwatts/$cm^2$ and exhibiting substantial intensity in the wavelength region of 400–500 nm.

In the above description, the high intensity light was directed for 20 seconds to each of the occlusal, facial, and lingual surfaces of the attachment to polymerize the resin and initiate sufficient cure to fix the interconnecting parts into an integral structure. Thereafter, the bridge was removed from the patient's mouth and the occlusal, facial, gingival, and lingual areas thereof re-exposed to the Prisma-Lite ® for 20 seconds to insure complete polymerization of the resin to form a fixedly bonded unitary structure. The bridge was then replaced in the patient's mouth and cemented to the abutment teeth.

We claim:

1. Fixed partial dentures consisting of abutment crowns and pontics connected through male/female attachments fixedly-joined into unitary structures, said female portions of said attachments having a location within the pontics of said dentures, and said male portions being integral with said crowns and having a length extending up to the entire mesial-distal length of the pontics of said dentures, said crowns and pontics being fixedly joined together by means of a joining medium selected from the group consisting of a time-setting material, a material curable through exposure to ultraviolet radiation, a material curable through exposure to visible light radiation, and a combination thereof.

2. Fixed partial dentures according to claim 1 wherein said male portions have a substantially cylindrical geometry and a length not exceeding about 75% of the mesial-distal length of said pontics.

3. Fixed partial dentures according to claim 1 wherein said material is a composite resin curable through exposure to visible light.

4. Fixed partial dentures according to claim 1 consisting of two parts fixedly joined together by a single male/female attachment.

5. Fixed partial dentures according to claim 1 consisting of three parts fixedly joined together by a single male/female attachment.

6. Fixed partial dentures according to claim 1 consisting of three parts fixedly joined together by two male/female attachments.

7. Fixed partial dentures according to claim 1 wherein said portions are fabricated from materials selected from the group consisting of metals, ceramics, plastics, and fiber reinforced glasses, glass-ceramics, and metals.

8. Fixed partial dentures according to claim 1 wherein said portions are fabricated from a glass-ceramic.

9. Fixed partial dentures according to claim 8 wherein said glass-ceramic is machinable and consists essentially, expressed in terms of parts by weight on the oxide basis, of

| $K_2O$ | 10–18 | $Al_2O_3$ | 0–2 |
|---|---|---|---|
| MgO | 14–19 | $ZrO_2$ | 0–7 |
| $SiO_2$ | 55–65 | F | 4–9 |

10. Fixed partial dentures according to claim 1 wherein said portions are fabricated from materials which permit the transmission therethrough of radiation selected from the group consisting of ultraviolet and visible light radiation.

11. A method for making fixed partial dentures consisting of abutment crowns and pontics fixedly joined into unitary structures by male/female attachments, said female portions of said attachments having a location within the pontics of said dentures, and said male portions being integral with said abutment crowns and having a length extending up to the entire mesial-distal length of the pontics of said dentures, which comprises the steps of:

(a) forming said parts into the desired shapes;

(b) providing joining medium to said male/female attachments by means selected from the group consisting of inserting a joining medium within said female pontics and applying a joining medium to said male portions, said joining medium being selected from the group consisting of a time-setting material, a material curable through exposure to ultraviolet radiation, a material curable through exposure to visible light radiation, and a combination thereof;

(c) assembling said parts together including, introducing said male portions into said female portions; and (d) curing said joining medium to fixedly join together said parts.

12. A method according to claim 11 wherein said male portions have a substantially cylindrical geometry and a length not exceeding about 75% of the mesial-distal length of said pontics.

13. A method according to claim 11 wherein said material is a composite resin curable through exposure to visible light.

14. A method according to claim 11 wherein said dentures consist of two parts fixedly joined together by a single male/female attachment.

15. A method according to claim 11 wherein said dentures consist of three parts fixedly joined together by a single male/female attachment.

16. A method according to claim 11 wherein said dentures consist of three parts fixedly joined together by two male/female attachments.

17. A method according to claim 11 wherein said portions are fabricated from materials selected from the group consisting of metals, ceramics, plastics, and fiber reinforced glasses, glass-ceramics, and metals.

18. A method according to claim 11 wherein said portions are fabricated from a glass-ceramic.

19. A method according to claim 18 wherein said glass-ceramic is machinable and consists essentially, expressed in terms of parts by weight on the oxide basis, of:

| $K_2O$ | 10–18 | $Al_2O_3$ | 0–2 |
|---|---|---|---|
| MgO | 14–19 | $ZrO_2$ | 0–7 |
| $SiO_2$ | 55–65 | F | 4–9 |

20. A method according to claim 11 wherein said portions are fabricated from materials which permit the transmission therethrough of radiation selected from the group consisting of ultraviolet and visible light radiation.

* * * * *